(12) United States Patent
Kerr (10) Patent No.: US 11,397,172 B2
(45) Date of Patent: Jul. 26, 2022

(54) DETERMINING THE PARTIAL PRESSURE OF A GAS, CALIBRATING A PRESSURE SENSOR

(71) Applicant: FATHOM SYSTEMS LIMITED

(72) Inventor: Gareth Kerr, Portlethen (GB)

(73) Assignee: JFD LIMITED, Aberdeen (GB)

( * ) Notice: Subject to any disclaimer, the term of this patent is extended or adjusted under 35 U.S.C. 154(b) by 0 days.

(21) Appl. No.: 16/988,961

(22) Filed: Aug. 10, 2020

(65) Prior Publication Data

US 2020/0371078 A1  Nov. 26, 2020

Related U.S. Application Data

(62) Division of application No. 15/542,727, filed as application No. PCT/GB2016/050075 on Jan. 13, 2016, now Pat. No. 10,768,152.

(30) Foreign Application Priority Data

Jan. 13, 2015 (GB) ...................................... 1500519

(51) Int. Cl.
*G01N 33/00* (2006.01)
*A61G 10/02* (2006.01)

(52) U.S. Cl.
CPC ....... *G01N 33/0006* (2013.01); *A61G 10/023* (2013.01); *A61G 2203/34* (2013.01)

(58) Field of Classification Search
CPC ........ G01N 7/00; G01N 15/0618; G01N 1/24; G01N 2001/2223; B01D 46/446
USPC ...................................................... 73/28.03
See application file for complete search history.

(56) References Cited

U.S. PATENT DOCUMENTS

| | | | | |
|---|---|---|---|---|
| 3,442,773 A | * | 5/1969 | Wilson | G01N 27/4067 205/785 |
| 3,587,438 A | * | 6/1971 | Foster | B64D 13/04 454/70 |
| 3,593,735 A | * | 7/1971 | Reiher | A62B 7/14 137/88 |
| 3,794,059 A | * | 2/1974 | Burt, Jr. | G05D 16/2013 137/93 |

(Continued)

FOREIGN PATENT DOCUMENTS

| | | |
|---|---|---|
| CN | 103884750 | 6/2014 |
| EP | 0270088 | 6/1988 |

(Continued)

*Primary Examiner* — Clayton E. LaBalle
*Assistant Examiner* — Warren K Fenwick
(74) *Attorney, Agent, or Firm* — Lundeen & Lundeen PLLC; Daniel N. Lundeen (57) ABSTRACT

There is disclosed a method and system for determining the partial pressure of at least one gas in a mixture of gasses contained in a pressure vessel, the mixture being pressurised to a level which is above local atmospheric pressure. The method comprises the steps of positioning a gas analysis sensor (14) within a pressure vessel (10); exposing the sensor to the mixture of gasses at the pressure level found in the pressure vessel; operating the sensor to measure the actual partial pressure of the at least one gas in the mixture contained in the vessel; and periodically calibrating the sensor by directing a calibrating gas mixture (20, 22) to the sensor in the chamber, the calibrating gas mixture being breathable by a human being.

19 Claims, 5 Drawing Sheets

(56) References Cited

U.S. PATENT DOCUMENTS

| | | | | |
|---|---|---|---|---|
| 3,824,157 A * | 7/1974 | Macur | | A61B 5/14539 205/782.5 |
| 4,407,153 A * | 10/1983 | Furlong | | G01N 7/00 128/204.24 |
| 4,939,647 A * | 7/1990 | Clough | | B63C 11/24 128/201.27 |
| 5,583,282 A * | 12/1996 | Tom | | G01N 29/02 73/31.03 |
| 5,924,418 A * | 7/1999 | Lewis | | B63C 11/24 128/204.22 |
| 6,003,513 A * | 12/1999 | Readey | | A62B 9/022 128/202.22 |
| 6,302,106 B1 * | 10/2001 | Lewis | | B63C 11/24 128/204.22 |
| 6,378,372 B1 * | 4/2002 | Karr | | G01N 29/036 73/24.01 |
| 8,800,344 B2 * | 8/2014 | Stone | | A61M 16/12 73/1.06 |
| 2004/0107965 A1 * | 6/2004 | Hickle | | A61M 16/203 128/204.22 |
| 2008/0000471 A1 * | 1/2008 | Bolam | | A61M 16/12 128/200.24 |
| 2012/0325207 A1 * | 12/2012 | Fromage | | A61M 16/026 128/203.14 |
| 2019/0358472 A1 * | 11/2019 | Gauthier | | A62B 7/02 |

FOREIGN PATENT DOCUMENTS

| | | |
|---|---|---|
| GB | 2094483 | 9/1982 |
| WO | 2008055167 | 5/2008 |

* cited by examiner

DETERMINING THE PARTIAL PRESSURE OF A GAS, CALIBRATING A PRESSURE SENSOR

The present invention relates to a method and system for determining the partial pressure of at least one gas in a mixture of gasses contained in a pressure vessel. The present invention also relates to a method of calibrating a gas analysis sensor used to measure the partial pressure of at least one gas in a mixture of gasses contained in a pressure vessel.

Divers operating at depth in a body of water experience elevated pressures. On average, the pressure in a body of water increases by 1 atmosphere (atm), or 1.01325 bar, for every 10 metres sea water (msw) in depth. Consequently, a diver operating at a depth of 100 msw will experience a pressure of 10 atm (10.1325 bar), at 200 msw a pressure of 20 atm (20.265 bar), and so on.

Under pressure at depth, increased volumes of gasses pass into solution in a diver's body. This effect tends to occur at an exponential rate depending upon the difference between the external gas partial pressures, the solubility of the breathed gasses and the partial pressures of the gases already dissolved in the body.

Divers have to ascend from depth slowly and, depending upon their depth and time of exposure to pressure, often have to stop at particular depths during their ascent to the surface. These stops, coupled with slow ascent, enable the dissolved gasses to come out of solution through the lungs, and the differential pressures between the dissolved gases in the diver's body and the external pressure is sufficiently low so that damaging bubbles do not form in the body.

When 'saturation' diving, divers have to remain at pressure for the entire duration of the dive, which may last for several weeks. To accomplish this, the divers live in pressurised chambers on the surface, and are transported to and from depth in a pressurised diving bell. A single process of stops and ascent occur at the end of the saturation dive. This is more efficient than doing a series of repeated short duration dives, where the combined durations of decompression would be much greater.

Atmospheric air is a mixture of gasses, which typically contains approximately 78% Nitrogen ($N_2$) and 21% Oxygen ($O_2$), The partial pressure of each gas in the mixture is the hypothetical pressure of that gas if it alone occupied the volume of the mixture at the same temperature. Accordingly, at a standard surface pressure of 1 atm, the partial pressure of $O_2$ is typically 0.21 atm or ~0.20265 bar. At a depth of 100 msw, the partial pressure of $O_2$ would therefore be 2.1 atm (~2.0265 bar), and at 200 msw would be 4.2 atm (~4.053 bar).

Divers operating at shallow depths for short periods employ a breathing gas which is often simply compressed air. However, divers descending to greater depths, and/or operating underwater for longer periods, have to use specialised breathing gas mixtures. This is because $N_2$ under pressure has a narcotic effect (commencing at a depth of around 40 m), and so Helium (He) is used. Also, $O_2$ is toxic at elevated partial pressures, depending upon the length of exposure and the partial pressure. For long term exposures, the partial pressure of $O_2$ must be kept to below 0.5 bar, and typically in the range of 0.44 to 0.48 bar during storage in a pressure chamber, and 0.40 to 0.60 bar for in-water excursions of a few hours. Carbon Dioxide ($CO_2$) must be kept to below 0.005 bar, above which level the gas is toxic. Other gases may be present in trace amounts that should be measured, including Carbon Monoxide, residual Nitrogen and Argon.

Divers have to spend significant amounts of time under pressure in the water and inside pressure chambers, during rest periods between deployment underwater, and also during subsequent decompression. When under pressure, the constituents of divers' breathing gas have to be kept within accurate limits, in order to avoid the problems discussed above. Since the partial pressure of the gasses is related to the pressure in the chamber and the proportion of the gas in the breathing mixture, at high pressures the actual proportion of gas (to be measured) in the mixture can be very small. For example, a diver operating at a depth of 100 msw (i.e. 10.1325 bar) for a sustained period will be provided with breathing gas in which the partial pressure of $O_2$ at that depth will be kept to around 0.48 bar, as discussed above. As a result, at surface atmospheric pressure, the partial pressure of $O_2$ in the mixture will be only 0.0474 bar by volume, which equates to just ~4.74% of the total. For a depth of 200 msw (20.265 bar), the partial pressure of $O_2$ will be only 0.0237 bar, equating to just ~2.37%, by volume, of the total. This presents a significant problem to the safe operation of diving systems, because the partial pressures of the gasses in the breathing mixture must be accurately measured, so that the relative proportions of the gasses can be accurately controlled.

In particular, the sensors have to be calibrated regularly, typically twice per day. Usually this is done with a two-point calibration, using two special calibration gasses/gas mixtures that are fed to the sensor. "Zero gas" contains the inert gas that the divers are breathing, has none of the gas to be measured (in the mixture in the chamber), and is used to calibrate a zero point output of the analyser. "Span gas" contains the inert gas that the divers are breathing and has the desired maximum value of the gas to be measured in the mixture. This is used to calibrate a desired maximum point output of the analyser. For example at a depth of 100 msw (10 bar) this might be 5% Oxygen with the balance inert gas. This gives a partial pressure of 0.5 bar at that depth, which is higher than the desired control limit but safe for the divers to breathe.

The problem is that health & safety regulations dictate that only breathable gas mixtures are allowed inside the chamber. Consequently, "zero gas" cannot be supplied into the chamber to calibrate the sensor. This means that the sensor has to be located outside the chamber. Prior to passing through the sensor, the breathing gas mixture is de-pressurised to local atmospheric pressure. The difficulty here is that the raw outputs from the sensors used to measure $O_2$ and $CO_2$ are proportional to the partial pressure of the gas in the mixture measured at the sensor (at atmospheric pressure), and if proportional (percentage) readings are required corresponding to the partial pressure of that gas in the chamber, the partial pressure value has to factored to eliminate the effects of pressure.

Using an extreme example of a working pressure equivalent to 300 msw (30 atm or 30.3975 bar), and using the maximum allowable $CO_2$ partial pressure given above (0.005 bar), the measured partial pressure of $CO_2$ in the breathing gas mixture at atmospheric pressure will be just 0.00016 bar (or ~0.016% by volume of the mixture total, at atmospheric pressure). The partial pressure band for oxygen would be measured to be just 0.015 bar to 0.016 bar (or ~1.48% to 1.58% $O_2$ by volume of the mixture total, at atmospheric pressure). This is a significant problem because, in order to accurately measure the proportions of $CO_2$ and $O_2$ in the mixture, sensor resolution and accuracy needs to be superior to the magnitude of the quantity being measured. In addition, typical sensors may only have an accuracy of only around ±2%, with the result that they cannot accurately measure the proportions of $CO_2$ and $O_2$ in the mixture.

From the above, it can be seen that diver safety depends upon being able to measure these partial pressures very accurately. It can also be seen that the requirement for accuracy becomes more onerous as pressure increases, and that for deep (high pressure) diving, very accurate instruments are needed.

Whilst reference is made particularly to problems associated with divers operating under pressure at depth, it will be understood that the problems associated with working under pressure, and the safe operation of pressure chambers, is not restricted to divers. Many other workers operate at pressure, including but not restricted to construction workers operating at elevated pressures in caissons and tunnels. Pressure chambers are also commonly used in the healthcare industry, for a variety of hyperbaric treatments.

It is amongst the objects of the present invention to obviate or mitigate at least one of the foregoing disadvantages.

According to a first aspect of the present invention, there is provided a method of determining the partial pressure of at least one gas in a mixture of gasses contained in a pressure vessel, the mixture being pressurised to a level which is above local atmospheric pressure, in which the method comprises the steps of:
   positioning a gas analysis sensor within the pressure vessel;
   exposing the sensor to the mixture of gasses at the pressure level found in the pressure vessel;
   operating the sensor to measure the actual partial pressure of the at least one gas in the mixture contained in the vessel; and
   periodically calibrating the sensor by directing a calibrating gas mixture to the sensor in the chamber, the calibrating gas mixture being breathable by a human being.

According to a second aspect of the present invention, there is provided a method of calibrating a gas analysis sensor used to measure the partial pressure of at least one gas in a mixture of gasses contained in a pressure vessel, the mixture being pressurised to a level which is above local atmospheric pressure, the method comprising the steps of:
   positioning the sensor within the pressure vessel;
   coupling the sensor to a calibrating assembly comprising a source of a calibrating gas mixture which is breathable by a human being, the source being located outside the vessel; and
   selectively operating the calibrating assembly to supply the calibrating gas mixture from the source to the sensor in the vessel, to calibrate the sensor.

Advantageously, in the methods of the first and second aspect of the present invention, the use of a calibrating gas mixture which is breathable by a human being enables the sensor to be positioned inside the pressure vessel. In this way, the partial pressure measurement of the target gas (or gasses) can be carried out within the pressure vessel itself. Consequently, the sensor measures the actual partial pressure of the target gas (or gasses). This is in significant contrast to prior methods, in which the sensor is located outside of the pressure vessel, the pressure of the gas mixture to be analysed being reduced to local atmospheric level, and the partial pressure measurement then carried out (and subsequently factored to account for the measurement at this reduced level, with consequent inaccuracies).

Reference is made herein to a calibrating gas mixture which is 'breathable' by a human being. This should be taken to mean that the calibrating gas comprises a mixture of gasses which, when breathed by a human being, is capable of supporting the life of that person. Accordingly, the gas mixture should be understood to comprise $O_2$; and not to contain any gasses which would be toxic if breathed by a human being and/or not to contain gasses in proportions which, at the prevailing pressure found in the pressure vessel, would be either substantially immediately toxic to human beings or which would be toxic following extended exposure (e.g. over a time period of the order of several hours or days).

During calibration, the sensor may be operated to determine the partial pressure of at least one calibrating gas in the calibrating gas mixture directed/supplied to the sensor.

The step of calibrating the sensor/calibration may comprise:
   supplying a low point calibration gas mixture to the sensor comprising a known first proportion of a calibration gas;
   monitoring a partial pressure value of the calibration gas outputted by the sensor;
   comparing the partial pressure value of the calibration gas outputted by the sensor to the actual partial pressure value which the sensor should output for said proportion of calibration gas at the pressure in the pressure vessel at which the measurement is made;
   determining any deviation between said values; and
   calibrating the sensor to account for any such deviation.

The step of calibrating the sensor may comprise:
   supplying a high point calibration gas mixture to the sensor comprising a known second proportion of a calibration gas, the second proportion being higher than the first proportion;
   monitoring the partial pressure value of the calibration gas outputted by the sensor;
   comparing the partial pressure value of the calibration gas outputted by the sensor to the actual partial pressure value which the sensor should output for said proportion of calibration gas at the pressure in the pressure vessel at which the measurement is made;
   determining any deviation between said values; and
   calibrating the sensor to account for any such deviation.

It will be understood that the low point calibration gas mixture will typically be supplied to the sensor first, followed by the high point calibration gas mixture. However, the high point calibration gas mixture may be supplied first, followed by the low point calibration gas mixture. The references to first and second proportions of calibration gas should be interpreted with this in mind. Specifically, in this scenario, the high point calibration gas mixture will then contain a known first proportion of calibrating gas, and the low point calibration gas mixture will contain a known second proportion of calibrating gas which is lower than the first proportion.

The low point and high point calibration gas mixtures, being breathable gasses, will contain $O_2$ in known proportions. Suitably therefore, the calibration gas is $O_2$. However, it will be understood that the calibration gas may be any other constituent gasses of the mixtures. The first and second proportions of the calibration gas may be selected depending upon the gas, and the pressure in the pressure vessel containing the sensor.

For example, where the calibration gas is $O_2$, the first proportion of $O_2$ in the low point calibration gas mixture may be selected so that the partial pressure of the gas in the calibration gas mixture, at the pressure in the vessel, is around 0.1.5 bar. This is equivalent to breathing air at an altitude of around 5,500 m and is a safe low point level for supporting human life. By way of example, at a pressure of 100 msw in the vessel, an $O_2$ partial pressure of 0.15 bar would be equivalent to 0.015 bar at (typical) local atmospheric pressure, and so a proportion of 1.5% $O_2$ by volume in the mixture at atmospheric pressure. The second proportion of $O_2$ in the high point calibration gas mixture may be selected so that the partial pressure of the gas in the calibration gas mixture, at the pressure in the vessel, is around 0.60 bar. This is a safe high point level of $O_2$ that a human being can be exposed to for a period of several hours. By way of example, at a pressure of 100 msw in the vessel, an $O_2$ partial pressure of 0.60 bar would be equivalent to 0.06 bar at (typical) local atmospheric pressure, and so a proportion of 6% $O_2$ by volume in the mixture at local atmospheric pressure.

The step of calibrating the sensor may comprise:
progressively varying the proportion of the calibrating gas in the calibrating gas mixture directed to the sensor between the first proportion and the second proportion;
monitoring the sensor output during the period that the proportion of said calibrating gas is varied;
comparing the partial pressure values of the calibration gas outputted by the sensor to the actual partial pressure values which the sensor should output for said proportion of calibration gas at the pressure in the pressure vessel at which the measurement is made;
determining any deviation between said values; and
calibrating the sensor to account for any such deviation.

As is known in the industry, sensor deviation can occur both as a fixed deviation (+/−) from the actual partial pressure, and as a 'drift' (+/−) which increases with pressure (and so resulting in a greater deviation at higher partial pressures than at lower partial pressures of the calibration gas). Varying the partial pressure of the calibrating gas in this way may therefore provide a dynamic indication of any sensor drift, so that an appropriate calibration can be made.

The step of calibrating the sensor may comprise directing a pre-prepared calibration gas mixture to the sensor, said pre-prepared mixture comprising a determined proportion of a calibrating gas. Where low point and high point calibrating gas mixtures are directed to the sensor, two separate sources of pre-prepared mixtures may be directed to the sensor. The proportion of calibrating gas in the calibrating gas mixture may be varied by controlling the flow of low and high point calibrating gas mixtures to the sensor.

The method may comprise preparing the calibrating gas mixture by mixing the calibrating gas with at least one further gas, and progressively varying the proportion of the calibrating gas in the mixture. This may be achieved by providing a source of calibrating gas and a separate source (or sources) of the at least one further gas, and mixing a flow of gas from the source of calibrating gas and a flow of gas from the source of the at least one further gas, using flow control equipment. For example, the calibrating gas may be $O_2$ stored in a calibrating gas container and the further gas (providing the balance) may be He stored in a balance container.

A remainder (or balance) of the low and high point calibration gas mixtures may be an inert gas, in particular He, or a plurality of inert gasses of known proportions. The inert gas (or one of the inert gasses) may be employed as the calibration gas.

The step of positioning the sensor within the vessel may comprise locating the sensor within a container defining a sensor chamber, and arranging the sensor chamber so that it can communicate with the mixture of gasses in the pressure vessel. The step of calibrating the sensor may comprise flooding the sensor chamber with the calibration gas mixture to expel all (or a majority) of the vessel mixture from the sensor chamber. In this way, the sensor is entirely (or substantially entirely) exposed to the calibrating gas mixture. As the calibrating gas mixture is breathable, the calibrating gas mixture can be allowed to simply vent into the pressure vessel.

The step of calibrating the sensor may comprise directing the calibrating gas mixture into the vessel along a conduit having an outlet which communicates with an interior of the vessel (optionally with the sensor chamber defined by the container), and arranging the outlet so that it directs the mixture towards an inlet of the sensor. This may serve to flood the sensor inlet with the calibrating gas mixture. The outlet may be arranged to direct a jet of calibrating gas mixture towards the sensor inlet.

The method may comprise determining the partial pressures of a plurality of gasses in the mixture of gasses in the vessel. The sensor may be used to measure the partial pressures of a plurality of gasses, or a plurality of sensors may be employed, each sensor measuring the partial pressure of a single gas. Where there are a plurality of sensors, the method may comprise periodically calibrating each of the sensors. The sensors may be calibrated separately. Two or more sensors may be calibrated simultaneously. All of the sensors may be calibrated simultaneously. Flow control equipment may control the flow of calibrating gas mixture to the desired sensor(s).

The mixture of gasses in the pressure vessel may be a breathable mixture containing $CO_2$, $O_2$ and which may contain a diluent gas such as He, and other trace gases such as Carbon Monoxide, Nitrogen and Argon at very small concentrations. The method may comprise determining the partial pressures of $CO_2$, $O_2$, trace gases and/or the diluent gas in the mixture of gasses in the vessel.

The pressure vessel may be maintained at a substantially constant pressure over a determined period of time. Such may be the case where the pressure vessel is a pressure chamber providing life support for divers for long periods of time (of the order of days), in between periods where the divers operate underwater at depth. The pressure chamber may therefore be a life support pressure chamber, and may be a diving life support pressure chamber. The pressure chamber may be a diving bell.

The pressure chamber may additionally or alternatively function as a decompression chamber, in Which the pressure of the mixture of gasses in the chamber is reduced over time in a controlled fashion, employing the determined partial pressure data. Thus the method may comprise reducing the pressure of the mixture in the chamber over time, to decompress a person or persons (e.g. divers) from the raised pressure in the chamber (which is set according to the pressure under which the person has been operating) to local atmospheric pressure.

The pressure vessel may be a gas storage tank or cylinder, in particular a diving gas storage cylinder. The method may comprise directing the mixture of gasses in the cylinder to a diver, and may comprise performing a reduction in the pressure of the mixture of gases directed from the cylinder to the diver to a level which is determined according to an operating depth of the diver.

Determination of the actual partial pressure of the at least one gas in the mixture contained within the vessel (or other pressurised parts of a pressurised system including the vessel) may enable determination of the proportion of said gas in the mixture. The method may comprise determining the partial pressure of a plurality of gasses in the mixture, optionally of the gas or gasses making up a majority of the mixture. This may facilitate determination of the composition of the mixture of gasses contained in the vessel.

It will be understood that the calibrating step is typically carried out at determined time intervals, for example every 12 hours, especially when the pressure vessel is providing a life support function.

According to a third aspect of the present invention, there is provided a method of controlling the partial pressure of at least one gas in a mixture of gasses contained in a pressure vessel, the method comprising:
determining the partial pressure of the at least one gas in the mixture following the method of the first aspect of the present invention;
and then varying the proportion of the at least one gas in the mixture in the vessel in order to maintain the partial pressure of said gas within a target pressure range.

The method may be a method of providing life support for a person operating under pressure (e.g. underwater), in which the mixture of gasses in the chamber is a breathable mixture. The method may be a method of decompressing a person from a pressure which is above local atmospheric pressure (at which the person has been operating e.g. underwater) down to local atmospheric pressure. The method may be a method of providing life support for a person operating under pressure (e.g. underwater), in which the mixture of gasses is supplied, under pressure, to a person's breathing apparatus.

Further features of the step of determining the partial pressure of the at least one gas may be derived from the text set out above relating to the first aspect of the invention.

According to a fourth aspect of the present invention, there is provided a pressure vessel comprising a gas analysis system for determining the partial pressure of at least one gas in a mixture of gasses contained in the pressure vessel, the mixture being pressurised to above local atmospheric pressure, in which the system comprises:
a gas analysis sensor positioned within the pressure vessel and exposed to the mixture of gasses at the pressure level found in the pressure vessel, the sensor being operable to measure the actual partial pressure of the at least one gas in the mixture contained in the vessel; and
a calibrating assembly for calibrating the sensor, the calibrating assembly comprising a source of a calibrating gas mixture which is breathable by a human being, the source being located outside the vessel, in which the calibrating assembly is operable to selectively supply the calibrating gas mixture to the sensor in the vessel to calibrate the sensor.

The calibrating assembly may comprise a source of a low point calibration gas mixture, said mixture comprising a known first proportion of a calibration gas. The calibrating assembly may comprise a source of a high point calibration gas mixture, said mixture comprising a known second proportion of a calibration gas which is higher than the first proportion.

The calibrating assembly may be arranged to:
monitor a partial pressure value of the calibration gas outputted by the sensor;
compare the partial pressure value of the calibration gas outputted by the sensor to the actual partial pressure value which the sensor should output for said proportion of calibration gas at the pressure in the pressure vessel at which the measurement is made;
determine any deviation between said values; and
calibrate the sensor to account for any such deviation.

The calibration assembly may comprise a device for comparing the partial pressure values, determining any deviation and calibrating the sensor. The device may comprise a processor.

The calibrating assembly may be operable to:
progressively vary the proportion of the calibrating gas in the calibrating gas mixture directed to the sensor between the first proportion and the second proportion;
monitor the sensor output during the period that the proportion of said calibrating gas is varied;
compare the partial pressure values of the calibration gas outputted by the sensor to the actual partial pressure values which the sensor should output for said proportion of calibration gas at the pressure in the pressure vessel at which the measurement is made;
determine any deviation between said values; and
calibrate the sensor to account for any such deviation.

The calibration assembly may comprise a pre-prepared calibration gas mixture comprising a determined proportion of a calibrating gas. Where low point and high point calibrating gas mixtures are directed to the sensor, two separate sources of pre-prepared mixtures may be provided.

The calibration assembly method may be operable to prepare a calibrating gas mixture by mixing a calibrating gas with at least one further gas, and progressively varying the proportion of the calibrating gas in the mixture. This may be achieved by providing a source of calibrating gas and a separate source (or sources) of the at least one further gas, and flow control equipment for mixing a flow of gas from the source of calibrating gas and a flow of gas from the source of the at least one further gas.

The system may comprise a container defining a sensor chamber in which the sensor is located, the sensor chamber arranged so that it is in communication with the mixture of gasses in the pressure vessel. The calibration assembly may be arranged to flood the sensor chamber with the calibration gas mixture to expel all (or a majority) of the vessel mixture from the sensor chamber.

The calibration assembly may comprise a conduit for directing the calibrating gas mixture into the vessel, the conduit having an outlet which communicates with an interior of the vessel (optionally with the sensor chamber defined by the container). The outlet may be arranged to direct the mixture towards an inlet of the sensor. The outlet may be arranged to direct a jet of calibrating gas mixture towards the sensor inlet.

The pressure vessel may be operable to maintain the pressure of mixture at a substantially constant pressure over a determined period of time. The pressure vessel may be a pressure chamber, and may be a life support chamber, e.g. for divers operating at depth for long periods of time (of the order of days). The pressure chamber may be a diving life support pressure chamber. The pressure chamber may be a diving bell. The pressure chamber may additionally or alternatively function as a decompression chamber, in which the pressure of the mixture of gasses in the chamber can be reduced over time in a controlled fashion, employing the determined partial pressure data. The pressure vessel may be a gas storage cylinder or tank, in particular a diving gas storage cylinder.

According to a fifth aspect of the present invention, there is provided a gas analysis system for determining the partial pressure of at least one gas in a mixture of gasses contained in a pressure vessel, the mixture being pressurised to above local atmospheric pressure, the system having the features of the system which forms part of the pressure vessel of the fourth aspect of the invention.

Further features of the gas analysis system may be derived from the text set out above relating to the fourth aspect of the invention.

According to a sixth aspect of the of the present invention, there is provided a system for calibrating a gas analysis sensor used to measure the partial pressure of at least one gas in a mixture of gasses contained in a pressure vessel, the mixture being pressurised to a level which is above local atmospheric pressure, the gas analysis sensor being positioned within the pressure vessel so that it is exposed to the mixture of gasses at the pressure level found in the pressure vessel, the sensor being operable to measure the actual partial pressure of the at least one gas in the mixture contained in the vessel, in which the system comprises;

a calibrating assembly for calibrating the sensor, the calibrating assembly comprising a source of a calibrating gas mixture which is breathable by a human being, the source being located outside the vessel, the calibrating assembly being operable to selectively supply the calibrating gas mixture to the sensor in the vessel to calibrate the sensor.

Further features of the system may be derived from or with respect to any of the aspects of the invention set out above.

Embodiments of the present invention will now be described, by way of example only, with reference to the accompanying drawings, in which.

Figure 1:
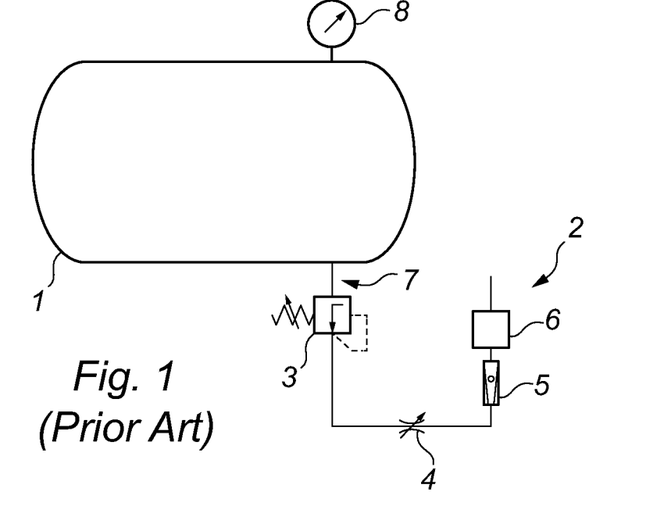
FIG. 1 is a schematic illustration of a pressure chamber with a gas analysis system of a type known in the art and which is employed to determine the partial pressure of a gas in a mixture of gases contained in the pressure chamber.

Turning firstly to FIG. 1, there is shown a schematic illustration of a pressure chamber 1 incorporating a gas analysis system. 2 of a type which is known in the art. The pressure chamber 1 is a life support chamber, containing a breathable mixture of gases at a pressure which is above local atmospheric pressure. The pressure chamber 1 provides life support for a person or persons who have been exposed to elevated pressures (above local atmospheric pressure) for relatively long periods of time, of the order of hours or days. Suitable examples include divers operating underwater at depths of up to around 200 msw, or even 300 msw with specialised diving equipment. The pressure chamber 1 can also be used as a decompression chamber, during subsequent decompression of a person or persons exposed to such elevated pressures.

The prior gas analysis system 2 comprises a pressure reducing valve 3, throttle valve 4, flow meter 5, gas analysis sensor 6, flow line 7 and pressure measurement device 8. The gas analysis system 2 is coupled to the pressure chamber 1 so that a portion of the mixture of gases can be exhausted from the chamber through the flow line 7, for direction to the sensor 6 for analysis. The pressure reducing valve 3 reduces the pressure of the mixture of gases directed to the sensor 6 to local atmospheric pressure level. The throttle valve 4 serves for throttling the flow of the mixtures of gases to a flow rate suitable for the gas analysis sensor 6, the flow being metered using the flow meter 5, to verify the flow rate is within a suitable range. The sensor 6 is responsive to partial pressure, and the output of the sensor is proportional to the percentage of the target gas present at atmospheric pressure. The pressure measurement device 8 is for determining the pressure inside the chamber 1, so that partial pressure inside the chamber can be calculated. The system 2 suffers from the significant disadvantages discussed above, in terms of the accuracy of the partial pressure measurement which is taken. This has a consequent impact upon the accuracy of the partial pressure of the gas in question at elevated pressure in the chamber 1, which is determined employing the measured partial pressure, factoring in the chamber pressure, as described in detail above.

Features of methods, systems and pressure vessels according to aspects of the present invention will now be described with reference to FIGS. 2 to 6 of the accompanying drawings.

Figure 2:
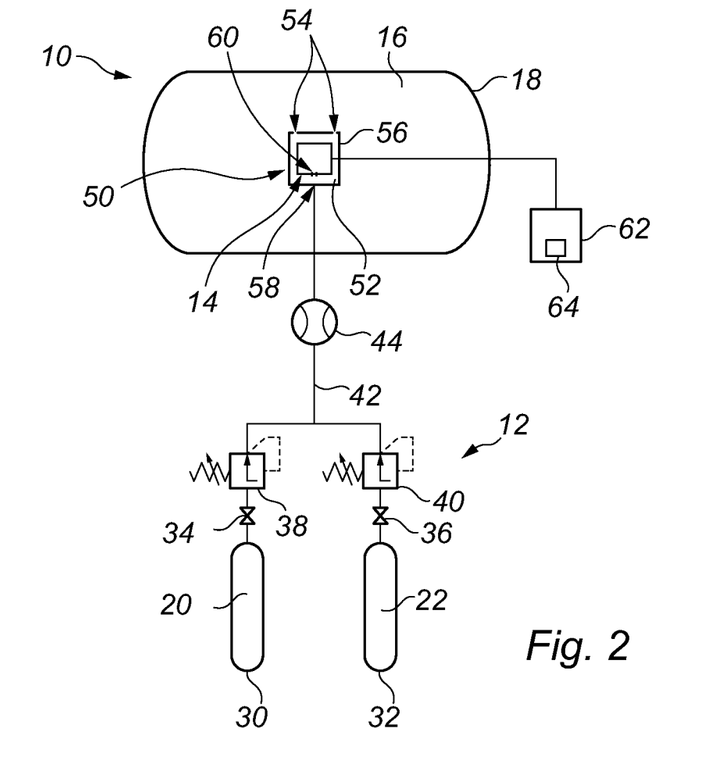
FIG. 2 is a schematic illustration of a pressure vessel, in the form of a pressure chamber, comprising a gas analysis system according to an embodiment of the present invention.

Thus turning now to FIG. 2, there is shown a schematic illustration of a pressure vessel in the form of a pressure chamber 10, having a gas analysis system indicated generally by reference numeral 12, according to an embodiment of the present invention. As with the prior chamber 1 and gas analysis system 2 of FIG. 1, the pressure chamber 10 provides a life support/decompression function, particularly for a diver. The gas analysis system 12 serves for determining the partial pressure of at least one gas in a mixture of gases contained in the pressure chamber 10, where the mixture is pressurised to above local atmospheric pressure.

The system 12 comprises a gas analysis sensor 14 which is responsive to partial pressure and which is located within the pressure chamber 10. Specifically, the sensor 14 is located within an internal void 16 defined by a wall 18 of the chamber 10. The sensor 14 is exposed to the breathable mixture of gases contained within the chamber 10, in the void 16, which are at the elevated pressure level. Since the sensor 14 is located within the chamber 10, it measures the actual partial pressure of the target gas, at the pressure of the mixture prevailing in the chamber. This overcomes difficulties associated with prior systems, such as the system 2 of FIG. 1, described above. In particular, measuring the partial pressure of the target gas at the elevated pressure level found within the chamber 10 avoids the inaccuracies which occurred in the prior system 2, due to the requirement to position the sensor 6 outside the chamber 1, and to reduce the pressure of the mixture of gases being analysed to local atmospheric pressure prior to measurement at the sensor 6.

The ability to locate the sensor 14 within the pressure chamber 10, and so to measure the actual partial pressure of the target gas, is facilitated by the gas analysis system 12. This is because the system 12 is arranged to periodically calibrate the sensor 14 by directing a calibrating gas mixture 20, 22 to the sensor 14 within the chamber 10, the calibrating gas mixture being one which is breathable by a human being. Previously and as described in relation to the prior gas analysis system 2 shown in FIG. 1, it was necessary to locate the sensor 6 outside the chamber 1 so that calibration could be effected. This was due to the use of a zero gas which was not breathable, in that it entirely comprised the inert gas that persons inside the chamber 1 were breathing (typically He), Thus by providing a calibrating gas mixture which is breathable, this allows the sensor 14 to be located within the pressure chamber 10.

It will be understood that the calibrating gas mixture is breathable in that it is capable of supporting the life of persons within the chamber 10. The calibrating gas mixture comprises $O_2$ and is typically a mixture of $O_2$ with a suitable inert balance gas such as helium, the mixture thus being "Heliox", which is well known in the industry. As will be described in more detail below, the proportion of $O_2$ in the calibrating gas mixture is carefully controlled.

Whilst reference is made herein to a method of determining the partial pressure of at least one gas in a mixture of gases contained in the pressure vessel 10, and to a corresponding system 12, the present invention also encompasses a method of calibrating a gas analysis sensor and a system for calibrating the sensor 14.

The systems and methods of the present invention will now be described in more detail.

As will be understood by person skilled in the art, gas analysis sensors such as the sensor 14 shown in FIG. 2 can provide partial pressure outputs suffering from one or both of fixed deviations (+/−) from the actual partial pressure of the target gas, and a phenomenon known as "drift" (+/−) in which a deviation from the actual partial pressure increases with pressure (resulting in a greater deviation at higher partial pressures than at lower partial pressures of the target gas).

In order to effectively ascertain both fixed deviations and drift, calibration of the sensor 14 is achieved by separately supplying a low point calibration gas mixture 20 to the sensor 14, and a high point calibration gas mixture 22 to the sensor. The low point calibration gas mixture 20 comprises a known first proportion of a calibration gas, which may be any suitable constituent of the gas mixture, but which may particularly be $O_2$. The high point calibration gas mixture 22 comprises a known second proportion of the calibration gas, the second proportion being higher than the first proportion.

The result of this is that the partial pressure of the calibration gas in the low point gas mixture 20, at the pressure prevailing in the chamber 10, is lower than the corresponding partial pressure of that calibration gas in the high point calibration gas mixture 22, Since the first and second proportions of the calibration gas in the low and high point mixtures 20 and 22 is known and indeed carefully controlled, the actual partial pressures of the calibration gas which should be outputted by the sensor 14 are known. Any deviations or drift of the calibration gas partial pressures outputted by the sensor 14 can therefore be determined and the sensor calibrated appropriately.

Figure 3:
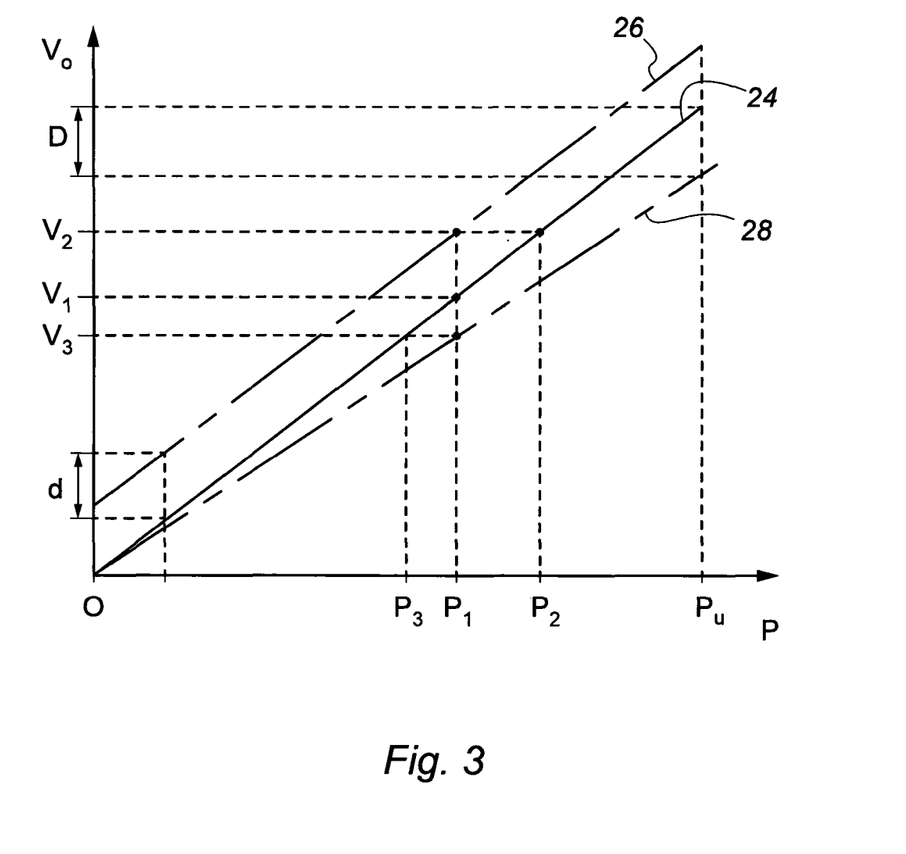
FIG. 3 is a graph illustrating output voltage readings ($V_o$) of a sensor forming part, of the gas analysis system of FIG. 2, indicative of a measured partial pressure of a target gas, against actual partial pressure of the gas, the graph showing possible deviations and drift from the actual partial pressure indicative of a sensor calibration requirement.

For example and turning to FIG. 3, there is shown a graph which is a plot of voltage output of the sensor 14 ($V_o$) against partial pressure (P) of the calibrating gas, which is suitably $O_2$ as discussed above (for a static partial pressure of the mixture containing the target gas).

The voltage output $V_o$ of the sensor 14 directly corresponds to the partial pressure of the gas being measured by the sensor (which under normal circumstances is a constituent of the mixture in the chamber 10, but during calibration is a constituent of the calibration gas mixture). The partial pressure P of the target gas is the actual partial pressure that the sensor should output for a particular, static pressure of the gaseous mixture being analysed. During calibration, the proportion of the target gas in the calibration gas mixture, and so the partial pressure P of the target gas, is known. In the illustrated example, the static pressure is that which would be experienced at 100 msw and so is 10 atm (10.325 bar).

The line 24 is a plot of the voltage $V_o$ Which a correctly functioning sensor 14 should output, as the partial pressure of the target gas (and thus the proportion of gas in the calibration gas mixture) increases from 0 to an upper level $P_u$. The line 26 is a plot of the voltage $V_o$ outputted by the sensor 14 which is indicative of a deviation 'd' from the actual partial pressure of the target gas (and thus from the line 24). The line 28 illustrates a situation in which the sensor 14 is experiencing a drift which increases with partial pressure of the target gas, the slope of the line 28 being different to that of the line 24. As can be seen, at the upper pressure $P_u$, the drift has resulted in a deviation 'D' in the partial pressure outputted by the sensor 14, compared to the actual partial pressure of the target gas (as indicated by the line 24).

This is best explained as follows, A correctly functioning sensor 14, as indicated by the line 24, outputs a voltage $V_1$ for a particular partial pressure $P_1$ of the target gas (say $O_2$). When the sensor 14 is experiencing a fixed deviation d (line 26), a voltage $V_2$ is actually outputted by the sensor, which corresponds to a partial pressure $P_2$ which is higher than the actual partial pressure $P_1$. In other words, the sensor 14 is providing a false higher indication of the partial pressure of $O_2$ than is actually the case. When the sensor 14 is experiencing a drift resulting in a deviation 1) (line 28), a voltage $V_3$ is actually outputted by the sensor, which corresponds to a partial pressure $P_3$ which is lower than the actual partial pressure $P_1$. In other words, the sensor 14 is providing a false lower indication of the partial pressure than is actually the case. It will be understood that this can be critical to the safety of persons in the chamber 10, when the sensor 14 is functioning to provide partial pressure measurements of $O_2$ (or other gasses) in the mixture in the chamber 10.

Supply of the low and high point calibration gas mixtures 20 and 22 to the sensor 14 is controlled by the gas analysis system 12. To this end, the system 12 comprises sources of low and high point calibrating gas mixtures in the form of high pressure storage cylinders 30 and 32. Valves 34 and 36 are associated with the respective cylinders 30 and 32, to select a gas output from the storage cylinders, Pressure regulators 38 and 40 are coupled to the respective valves 34 and 36 and, in conjunction with a flowmeter 44, control the flow and pressure of calibrating gas mixtures 20, 22 from the cylinders 30, 32. Typically, the pressure of the mixtures 20 and 22 will be controlled to be slightly above the pressure of the gaseous mixture in the chamber 10 (to provide a positive flow into the chamber), The calibrating gas mixture 20, 22 flows to the sensor 14 along a conduit 42, checked by the flowmeter 44.

Figure 4:
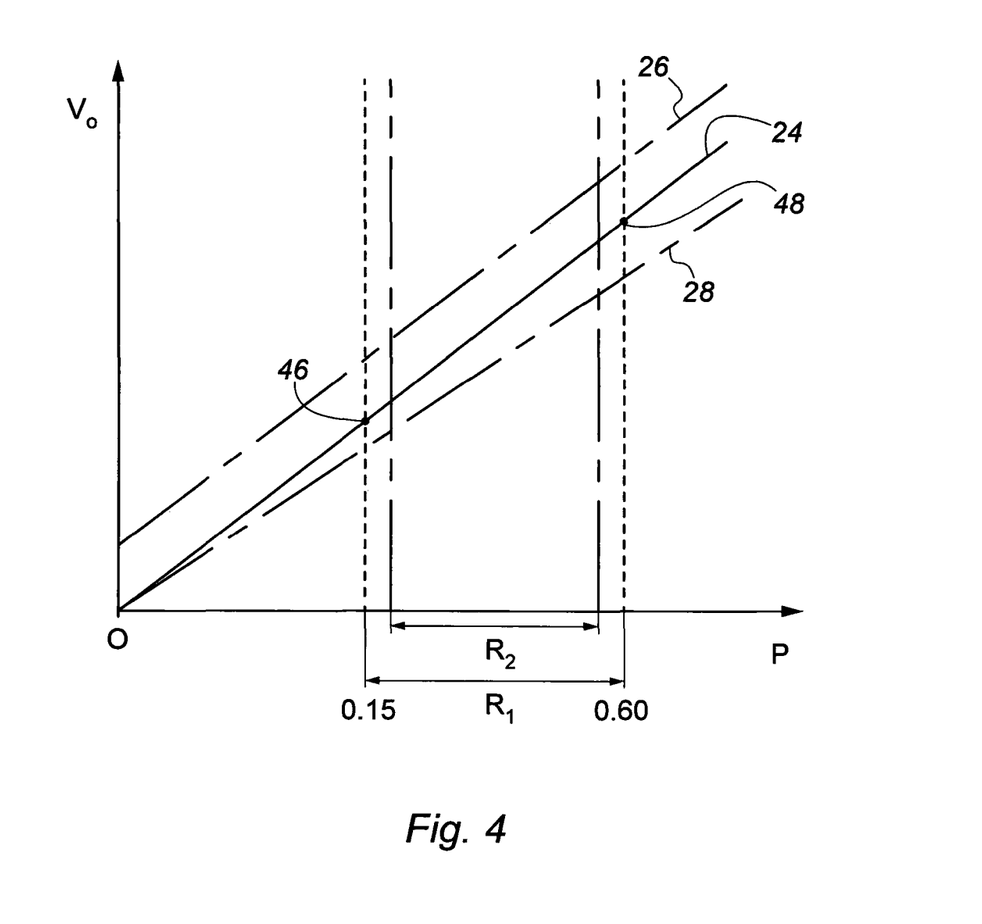
FIG. 4 is a graph similar to FIG. 3 illustrating voltage output readings ($V_o$) of the sensor against actual partial pressure of the gas, with safe and comfortable partial pressure ranges (for users of the pressure chamber) superimposed.

Typically, the low point calibration gas mixture 20 will be supplied to the sensor 14 first, followed by the high point calibration gas mixture 22. As described above, suitably the calibration gas forming part of the low and high point calibration gas mixtures 20 and 22 will be $O_2$. The proportion of $O_2$ in the low point calibration gas mixture 20 is selected so as to provide a partial pressure of $O_2$, at the pressure of the mixture in the chamber 10, of around 0.15 bar. This is equivalent to breathing air at an altitude of around 5,500 meters and is a safe low point for supporting human life. This is illustrated in FIG. 4, which is a graph similar to FIG. 3, where the low point level 46 is shown on the line 24. For measurements at 100 msw, the low point partial pressure $O_2$ of 0.15 bar is equivalent to 0.015 bar at local atmospheric pressure, and so a proportion of 1.5% $O_2$ by volume in the calibration gas mixture 20 at atmospheric pressure.

In the high point calibration gas mixture 22, a safe high point level of $O_2$ is selected to provide a partial pressure $O_2$ of around 0.60 bar at the pressure of the mixture in the chamber 10. A partial pressure $O_2$ of 0.60 bar is above a target range of 0.44 to 0.48 bar, but as described above, is acceptable for in-water excursions of a few hours and so represents a safe high point level 48.

The impact that a deviation d (line 26) or a drift resulting in a deviation D (line 28) in the sensor 14 output would have is illustrated in FIG. 4. In particular, a safe partial pressure range $R_1$, between the low and high point levels 46 and 48 is shown in the graph. This range $R_1$ encompasses a narrower pressure range $R_2$, which represents a more comfortable operating range of partial pressure $O_2$ for persons in the chamber 10.

A deviation d in the partial pressure $O_2$ outputted by the sensor 14, indicated by the line 26, will result in a partial pressure reading being outputted which is a significant magnitude higher than the actual partial pressure of $O_2$ in the chamber 10. This is critical at the lower end of the range $R_1$, because the sensor 14 could be indicating a partial pressure of $O_2$ which is at or above the low point level 46, but which is actually lower and insufficient to support persons in the chamber 10.

A drift resulting in a deviation D in the partial pressure $O_2$ measurement outputted by the sensor 14, indicated by the line 28, would in contrast result in a partial pressure reading being outputted which is a significant magnitude lower than the actual partial pressure of $O_2$ in the chamber 10. This is critical at the upper end of the range $R_1$, because the sensor 14 could be indicating a partial pressure of $O_2$ which is at or below the high point level 46, but which is actually higher and toxic to persons in the chamber 10.

In the illustrated embodiment, the system 12 comprises a container 50 which defines a sensor chamber 52 in which the sensor 14 is mounted. The sensor chamber 52 can communicate with the mixture of gases in the pressure chamber 10, contained in the void 16, suitably by way of apertures 54 in a wall 56 of the container 50. During calibration of the sensor 14, the sensor chamber 52 is flooded with the selected calibration gas mixture 20, 22, thereby expelling all (or a majority) of the gaseous mixture present in the chamber 10 from the sensor chamber 52. In this way, the sensor 14 is entirely or substantially entirely exposed to the selected calibrating gas mixture 20, 22. As the sensor chamber 52 is open to the chamber 10, the selected calibrating gas mixture 20, 22 (which is breathable) simply vents in to the chamber 10 through the apertures 54.

The conduit 42 along which the calibration gas mixture 20, 22 flows has an outlet 58 which communicates with the sensor chamber 52. The outlet 58 is arranged relative to an inlet 60 of the sensor 14 so that it directs the calibration gas mixture 20, 22 directly towards the sensor inlet 60. This may assist in flooding the sensor inlet 60 with the calibrating gas mixture 20, 22 and may enable the container 50 to be dispensed with.

The gas analysis system 12 comprises a device for comparing the partial pressure values, determining any deviation and automatically calibrating the sensor, the device indicated generally by reference numeral 62 and taking the form of a suitable processor. The processor 62 includes a display 64 for displaying the partial pressure measurements of the target gas outputted by the sensor 14. Automatic calibration of the sensor 14 is achieved by suitable software carried on the processor 62, of a type which is readily available in the industry.

Figure 5:
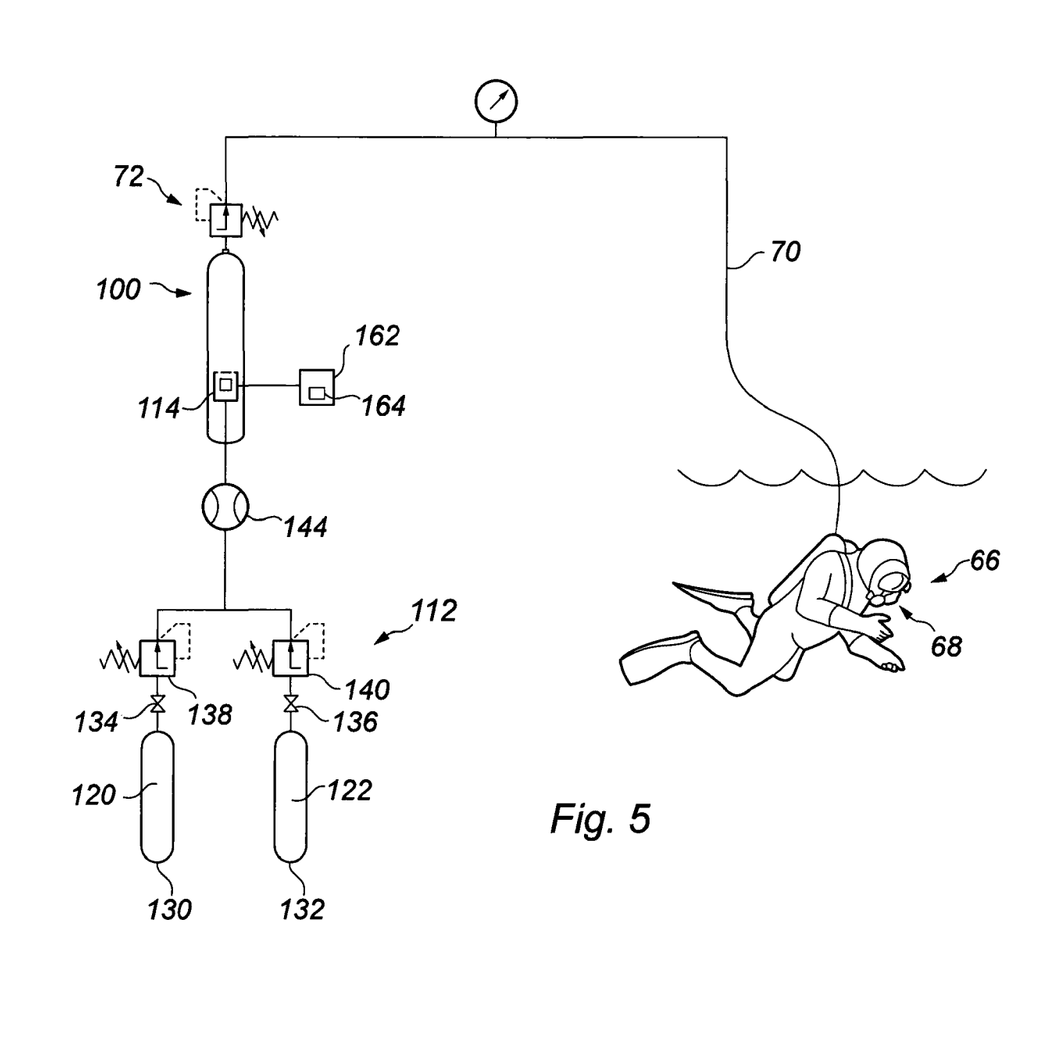
FIG. 5 is a schematic illustration of a pressure vessel, in the form of a gas storage cylinder coupled to a diver's breathing apparatus, and having a gas analysis system according to an embodiment of the present invention.

Turning now to FIG. 5, there is shown a schematic illustration of a pressure vessel and gas analysis system in accordance with another embodiment of the invention. The pressure vessel is designated by reference numeral 100, and takes the form of a gas storage cylinder or tank, which stores breathing gas for a diver 66, In this embodiment, the gas analysis system is indicated generally by reference numeral 112. Like components of the system 112 with the system 12 of FIG. 2 share the same reference numerals, incremented by 100.

The system 112 is essentially of like construction and operation to the system 12. The substantial difference between the embodiment of FIG. 5 and that of FIG. 2 is that, instead of monitoring the partial pressure of a target gas or gases within a pressure chamber suitable for receiving e.g. a diver 66, the system 112 monitors the partial pressure of a gas/gases in a mixture contained in the tank 100, which are supplied to breathing apparatus 68 worn by the diver 66 via a hose 70. The system 112 is used to test the breathing gas before it goes to the diver 66 in the water.

The breathing gas is stored in the tank 100, which is a high pressure cylinder, and the pressure is reduced by a pressure control device 72, in the form of a pressure regulator. This provides overpressure with respect to the hydrostatic pressure at the particular operating depth of the diver 66, matched to the requirement of the breathing apparatus 68 that the diver is using. As can be seen from the drawing, in this instance, a sensor 114 is provide in the tank 100, and the low and high point calibration gas mixtures 120 and 122 stored in respective cylinders 130 and 132. Valves 134 and 136 and regulators 138, 140, together with a flow meter 144, control the flow of the low and high point calibration gas mixtures 120, 122 to the sensor 114 to calibrate the sensor. Monitoring and calibration of the sensor 114 is performed by a processor 162, and partial pressures of target gas output on a display 164.

Figure 6:
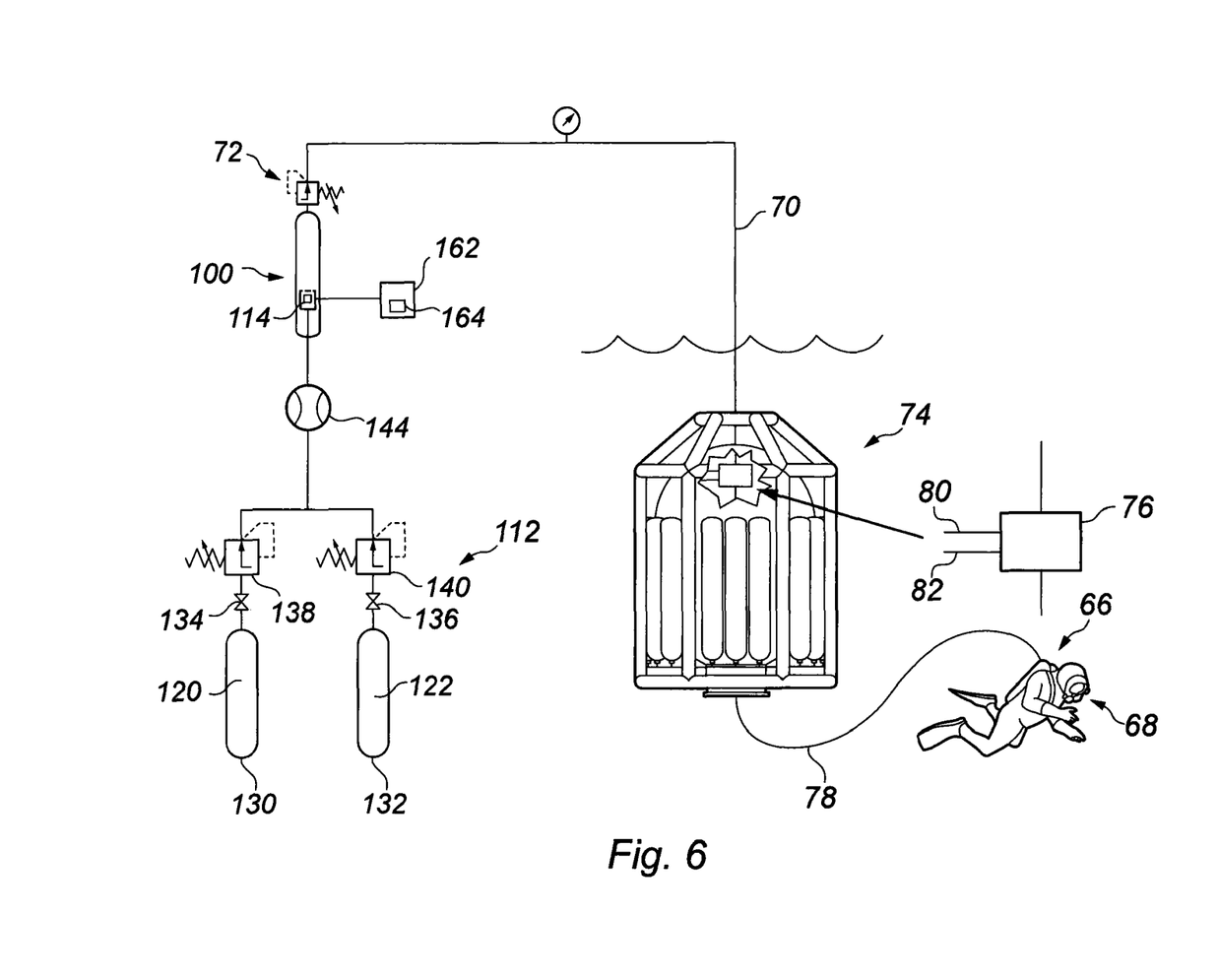
FIG. 6 is a schematic illustration of a pressure vessel, in the form of a gas storage cylinder coupled to a diving bell, and having the gas analysis system of FIG. 5.

FIG. 6 shows a variation of the system 112 shown in FIG. 5, in which the mixture of gases in the tank 100 is supplied to a diving bell 74 (through the hose 70), which provides life support for the diver 66 during deployment underwater. For example, the bell 74 can be used for transferring the diver 66 from a pressure chamber at surface (the pressure of the breathing mixture in the bell 74 being set at the same level as that in the chamber), as well as for providing underwater life support for the diver during times between excursions out of the bell and into the water.

Typically, the hose 70 is coupled to a gas panel 76 in the bell 74, which controls the supply of breathing gas both to an interior of the bell 74, and through a hose 78 to the breathing apparatus 68 worn by the diver 66. The gas panel 76 is also coupled to emergency breathing gas cylinders (not shown) via hoses 80 and 82, for supplying breathing gas to the interior of the bell 74 and/or to the diver 66 (via the hose 78) in the case of an emergency loss of supply of gas from the tank 100 at surface. From the above, it will be appreciated that the system 112 may effectively serve for monitoring the breathing gas supplied to both the bell 74 and to the diver's breathing apparatus 68.

Various modifications may be made to the foregoing without departing from the spirit or scope of the present invention.

The invention claimed is:

1. A method of calibrating a gas analysis sensor used to measure the partial pressure of at least one gas in a mixture of gasses contained in a pressure vessel, the mixture being pressurised to a level which is above local atmospheric pressure, the method comprising the steps of:
    positioning the sensor within the pressure vessel;
    coupling the sensor to a calibrating assembly comprising a source of a calibrating gas mixture which is breathable by a human being, the source being located outside the vessel, in which the calibrating assembly comprises a pre-prepared calibration gas mixture comprising a determined proportion of a calibrating gas; and
    selectively operating the calibrating assembly to supply the calibrating gas mixture from the source to the sensor in the vessel, to calibrate the sensor.

2. A pressure vessel comprising a gas analysis system for determining the partial pressure of at least one gas in a mixture of gasses contained in the pressure vessel, the mixture being pressurised to above local atmospheric pressure, in which the system comprises:
    a gas analysis sensor positioned within the pressure vessel and exposed to the mixture of gasses at the pressure level found in the pressure vessel, the sensor being operable to measure the actual partial pressure of the at least one gas in the mixture contained in the vessel; and
    a calibrating assembly for calibrating the sensor, the calibrating assembly comprising a source of a calibrating gas mixture which is breathable by a human being, the source being located outside the vessel, in which the calibrating assembly is operable to selectively supply the calibrating gas mixture to the sensor in the vessel to calibrate the sensor;
    in which the calibrating assembly comprises a pre-prepared calibration gas mixture comprising a determined proportion of a calibrating gas.

3. A pressure vessel as claimed in claim 2, in which the calibrating assembly comprises a source of a low point calibration gas mixture, said mixture comprising a known first proportion of a calibration gas.

4. A pressure vessel as claimed in claim 3, in which the calibrating assembly further comprises a source of a high point calibration gas mixture, said mixture comprising a known second proportion of a calibration gas which is higher than the first proportion.

5. A pressure vessel as claimed in claim 4, in which the calibrating assembly is operable to:
    progressively vary the proportion of the calibrating gas in the calibrating gas mixture directed to the sensor between the first proportion and the second proportion;
    monitor the sensor output during the period that the proportion of said calibrating gas is varied;
    compare the partial pressure values of the calibration gas outputted by the sensor to the actual partial pressure values which the sensor should output for said proportion of calibration gas at the pressure in the pressure vessel at which the measurement is made;
    determine any deviation between said values; and
    calibrate the sensor to account for any such deviation.

6. A pressure vessel as claimed in claim 4, in which the calibrating assembly comprises two separate sources of pre-prepared low and high point gas mixtures.

7. A pressure vessel as claimed in claim 4, in which the calibrating assembly is arranged to:
    monitor a partial pressure value of a calibration gas of the mixture outputted by the sensor;
    compare the partial pressure value of the calibration gas outputted by the sensor to the actual partial pressure value which the sensor should output for said proportion of calibration gas at the pressure in the pressure vessel at which the measurement is made;
    determine any deviation between said values; and
    calibrate the sensor to account for any such deviation.

8. A pressure vessel as claimed in claim 3, in which the calibrating assembly is arranged to:
    monitor a partial pressure value of a calibration gas of the mixture outputted by the sensor;
    compare the partial pressure value of the calibration gas outputted by the sensor to the actual partial pressure value which the sensor should output for said proportion of calibration gas at the pressure in the pressure vessel at which the measurement is made;
    determine any deviation between said values; and
    calibrate the sensor to account for any such deviation.

9. A pressure vessel as claimed claim 8, in which the calibrating assembly comprises a device for comparing the partial pressure values, determining any deviation and calibrating the sensor.

10. A pressure vessel as claimed in claim 8, in which the outlet is arranged to direct a jet of calibrating gas mixture towards the sensor inlet.

11. A pressure vessel as claimed in claim 2, in which the calibrating assembly is arranged to:
    monitor a partial pressure value of a calibration gas of the mixture outputted by the sensor;
    compare the partial pressure value of the calibration gas outputted by the sensor to the actual partial pressure value which the sensor should output for said proportion of calibration gas at the pressure in the pressure vessel at which the measurement is made;
    determine any deviation between said values; and
    calibrate the sensor to account for any such deviation.

12. A pressure vessel as claimed in claim 2, in which the calibrating assembly comprises a device for comparing the partial pressure values, determining any deviation and calibrating the sensor.

13. A pressure vessel as claimed in claim 2, in which the calibrating assembly is operable to prepare a calibrating gas mixture by mixing a calibrating gas with at least one further gas, and to progressively vary the proportion of the calibrating gas in the mixture.

14. A pressure vessel as claimed in claim 2, comprising a container defining a sensor chamber in which the sensor is located, the sensor chamber arranged so that it is in communication with the mixture of gasses in the pressure vessel.

15. A pressure vessel as claimed in claim 14, in which the calibrating assembly is arranged to flood the sensor chamber with the calibration gas mixture to expel vessel mixture from the sensor chamber.

16. A pressure vessel as claimed in claim 15, in which the calibrating assembly comprises a conduit for directing the calibrating gas mixture into the vessel, the conduit having an outlet which communicates with the sensor chamber, the outlet being arranged to direct the mixture towards an inlet of the sensor.

17. A pressure vessel as claimed in claim 14, in which the calibrating assembly comprises a conduit for directing the calibrating gas mixture into the vessel, the conduit having an outlet which communicates with the sensor chamber, the outlet being arranged to direct the mixture towards an inlet of the sensor.

18. A pressure vessel as claimed in claim 17, in which the outlet is arranged to direct a jet of calibrating gas mixture towards the sensor inlet.

19. A gas analysis system for determining the partial pressure of at least one gas in a mixture of gasses contained in a pressure vessel, the mixture being pressurised to above local atmospheric pressure, in which the system comprises:
- a gas analysis sensor adapted to be positioned within the pressure vessel and exposed to the mixture of gasses at the pressure level found in the pressure vessel, the sensor being operable to measure the actual partial pressure of the at least one gas in the mixture contained in the vessel; and
- a calibrating assembly for calibrating the sensor, the calibrating assembly comprising a source of a calibrating gas mixture which is breathable by a human being, the source adapted to be located outside the vessel, in which the calibrating assembly is operable to selectively supply the calibrating gas mixture to the sensor in the vessel to calibrate the sensor, in which the calibrating assembly comprises a pre-prepared calibration gas mixture comprising a determined proportion of a calibrating gas.

* * * * *